(12) United States Patent
Surana et al.

(10) Patent No.: US 11,060,056 B2
(45) Date of Patent: Jul. 13, 2021

(54) **METHOD OF PRODUCING HIGH AMOUNT OF ETHANOL AT HIGH TEMPERATURE BY MODIFIED YEAST STRAIN *SACCHAROMYCES CEREVISIAE***

(71) Applicant: Rajendra Surana, Chhattisgarh Raipur (IN)

(72) Inventors: Rajendra Surana, Chhattisgarh Raipur (IN); Shashikant Shingdilwar, Chhattisgarh Raipur (IN); Pushpa Agrawal, Chhattisgarh Raipur (IN)

(73) Assignee: Rajendra Surana

( * ) Notice: Subject to any disclaimer, the term of this patent is extended or adjusted under 35 U.S.C. 154(b) by 206 days.

(21) Appl. No.: 15/776,317

(22) PCT Filed: Aug. 4, 2016

(86) PCT No.: PCT/IN2016/050260
§ 371 (c)(1),
(2) Date: May 15, 2018

(87) PCT Pub. No.: WO2017/090055
PCT Pub. Date: Jun. 1, 2017

(65) Prior Publication Data
US 2018/0327709 A1 Nov. 15, 2018

(30) Foreign Application Priority Data
Nov. 25, 2015 (IN) .......................... 4425/MUM/2015

(51) Int. Cl.
*C12N 1/18* (2006.01)
*C12P 7/06* (2006.01)
*C12N 15/09* (2006.01)
*C12P 7/10* (2006.01)

(52) U.S. Cl.
CPC ............... *C12N 1/18* (2013.01); *C12N 15/09* (2013.01); *C12P 7/06* (2013.01); *C12P 7/10* (2013.01); *C12P 2203/00* (2013.01)

(58) Field of Classification Search
CPC .................................... C12N 1/18; C12P 7/06
See application file for complete search history.

(56) References Cited

U.S. PATENT DOCUMENTS

2012/0252681 A1 10/2012 del Cardayre et al.
2014/0342423 A1 11/2014 Parekh et al.

FOREIGN PATENT DOCUMENTS

| CN | 103232948 B | 7/2015 |
| EP | 2837698 A1 | 2/2015 |
| WO | 2014170330 A2 | 10/2014 |
| WO | 2014180820 A2 | 11/2014 |

OTHER PUBLICATIONS

Sridhar. BioresourTechnol. Jul. 2002;83(3): 199-202. Effect of UV radiation on thermotolerance, ethanol tolerance and osmotolerance of *Saccharomyces cerevisiae* VS1 and VS3 strains.*
Thammasittirong. Improvement of ethanol production by ethanol-tolerant *Saccharomyces cerevisiae* UVNR56. Springerplus. 2013; 2: 583. Published online Oct. 31, 2013.*
Torija MJ, et al., "Effects of fermentation temperature on the strain population of *Saccharomyces cerevisiae*.", Int J Food Microbiol. Jan. 15, 2003;80(1):47-53. (abstract only).
Morimura, et al., "Ethanol production by repeated-batch fermentation at high temperature in a molasses medium containing a high concentration of total sugar by a thermotolerant flocculating yeast with improved salt-tolerance", 1997, J. Fermen. Bioeng.83(3) 271-274 (abstract only).
Benjaphokee S, et al., "Highly efficient bioethanol production by a *Saccharomyces cerevisiae* strain with multiple stress tolerance to high temperature, acid and ethanol.", N Biotechnol. Feb. 15, 2012;29(3):379-86 (abstract only).
Lu Y, et al., "Improvement of robustness and ethanol production of ethanologenic *Saccharomyces cerevisiae* under co-stress of heat and inhibitors.", J Ind Microbiol Biotechnol. Jan. 2012;39(1):73-80 (abstract only).
Banat IM, et al., "Isolation of thermotolerant, fermentative yeasts growing at 52° C. and producing ethanol at 45° C. and 60° C.", World J Microbiol Biotechnol. May 1992;8(3):259-63 (abstract only).

* cited by examiner

*Primary Examiner* — Yong D Pak
(74) *Attorney, Agent, or Firm* — St. Onge Steward Johnston & Reens LLC

(57) ABSTRACT

The present invention relates to a modified yeast strain of *Saccharomyces cerevisiae* having MCC accession number 0069 with osmo-tolerant, thermo-tolerant, ethanol tolerant and self-flocculation properties. Further, the present invention relates to a method for obtaining modified yeast strain. The present invention also relates to a method of production of ethanol at high temperature using said yeast strain. The ethanol produced by the method disclosed in the present invention is used as fuel.

22 Claims, 5 Drawing Sheets

METHOD OF PRODUCING HIGH AMOUNT OF ETHANOL AT HIGH TEMPERATURE BY MODIFIED YEAST STRAIN *SACCHAROMYCES CEREVISIAE*

FIELD OF THE INVENTION

The present invention relates to a modified yeast strain *Saccharomyces cerevisiae* Devleela-1 deposited at IDA, Microbial Culture Collection, Pune, India, having an accession number MCC 0069 and a method of producing high amount of ethanol at high temperature by modified yeast strain. More specifically, modified yeast strain *Saccharomyces cerevisiae* produces ethanol at a temperature range of 25° C. to 44° C. in high concentration. The modified yeast strain is osmotolerant, ethanol tolerant, thermotolerant and self-flocculating.

BACKGROUND OF THE INVENTION

Depleting resource of fossil fuel has created a situation for the continuous and increasing demand for renewable energy. One of the most common sources of fuel is ethanol which is mixed with petrol. Ethanol is used by other industries and thus there is an increasing demand for ethanol. Several methods exist where either whole plant material or whole grain is converted into starch, which might be separated from the original source or the starch is directly converted to sugar before fermentation. Methods also exist where either molasses or sugarcane juice, beet root molasses is also used for fermentation to produce ethanol. Fermentation is then carried out using by different strains of yeast. In either case, it is important to have a strain of yeast which can produce large amount of ethanol in shortest possible time.

After fermentation, ethanol is distilled, purified, concentrated and dehydrated before being used either as fuel ethanol or as potable ethanol or for other industrial applications. Therefore, higher the concentration of ethanol in the fermentation broth lower will be the cost of downstream processing. A good recovery after fermentation also reduces the amount of affluent need to be processed before releasing it to environment. Therefore, a good commercial strain of yeast ought to produce high concentration of ethanol for which it should be able to grow at high concentration of sugar (osmo-tolerant), in the presence of high concentration of ethanol (ethanol tolerant), at high temperature (thermo-tolerant) and should be self flocculating. Thermo-tolerance of yeast strain is one of the most desirable property of any commercial/industrial yeast strain as the sugarcane growing regions all over the world have long season of high environmental temperature, therefore, having a yeast strain which produces high concentration of ethanol at high temperature will be a boon for ethanol industry.

Self flocculation is a desirable property of yeast for ethanol fermentation. Flocculation means that once fermentation or stirring is finished, most of microbe population will deposit at the bottom. Thus, self flocculation helps during distillation process. If the strain does not collect at the bottom then it tends to block the distillation column.

There are number of synergistic stress factors involved in ethanol production using yeast. Yeast grows at optimum temperature range of 25° C.-32° C. Above this range of temperature there is a depression in fermentation. High temperature cause a decrease in cell viability, as well as changes in mitochondria and fluidity of the plasma membrane and it also increases yeast sensitivity to lactic and acetic acids, which causes lower ethanol yields. Further, high ethanol can cause important metabolic changes in yeasts such as ATPase inhibition, denaturation of several glycolytic enzymes and changes in the cell wall.

The processes in ethanol production involves the use of molasses and sugarcane juice or other source of sugars such as plant materials or grains, their milling either wet or solid, converting starch and other lignocellulosic material from these raw materials to sugar and then using yeast strain to convert sugars into ethanol by the process of fermentation at room temperature is well documented in the literature. However, there are challenges involved at high temperature.

Efforts are made by all skilled in the art to improve the process of ethanol fermentation by improving the properties of yeast strain to be used and sometimes by modifying the process of fermentation (Benjaphokee et. al., 2012 N. Biotechnol. 29(3)379-386; Lu et al., 2012, J. Ind. Microbiol. Biotechnol 0.39(1) 73-80; Morimura et. al., 1997, J. Fermen. Bioeng. 83(3) 271-274; Banat et al., 1992, W. J. Microbiol. Biotechnol. 8(3)259-263). It is estimated that even 1% increase in ethanol yield generates a commercial value of $100 million annually to ethanol industry. Article titled "Effects of fermentation temperature on the strain population of *Saccharomyces cerevisiae*" by Torija M J, International Journal of Food Microbiology 2003 Jan. 15; 80(1): 47-53 reports that viability of yeast cells decreased at high temperature, especially at 35° C. It also reported that yield of alcohol is lower at high temperature due to inhibitory effect of ethanol at increased temperature.

Patent CN 103232948 B discloses a high temperature resistant strain of *Saccharomyces cerevisiae* and breeding methods. The cited document discloses ethanol yield of 3.9% (v/v) at high temperature of 38° C. Further, it discloses ethanol yield of 12.2% (v/v) at high temperature of 40° C. WO 2014/170330 discloses yeast alleles involved in maximal alcohol accumulation capacity and tolerance to high alcohol levels.

EP2837698A1 discloses *Saccharomyces cerevisiae* strain having ethanol tolerance in concentrations between 14% (v/v)-16% (v/v). This strain can be used in food production by fermentation (including beverages), preferably obtained by musts fermentations such as wine, beer or cider. The fermentation is conducted at a temperature in the range from 16° C. to 28° C.

WO2014180820 A2 discloses yeast cell that is genetically modified having an osmotolerance of 0.5 OsM or more.

Therefore, there is a need in the art to develop a modified yeast strain producing high amount of ethanol having properties such as thermotolerance, osmotolerance, ethanol tolerance which self flocculates. Improved method for ethanol production providing increased concentration of ethanol has significant economic, environmental and industrial advantages.

OBJECTIVES OF THE INVENTION

The main objective of the present invention is to provide a modified yeast strain *Saccharomyces cerevisiae* having MCC accession number 0069 and having properties such as thermotolerance, osmotolerance, ethanol tolerance and self flocculation.

Another objective of the present invention is to provide a method for ethanol production by modified yeast strain.

Still another objective of the present invention is to provide a method for obtaining modified yeast strain.

Yet another objective of the present invention is to provide a method for ethanol production to be used as fuel, solvent, potable ethanol and for industrial application.

SUMMARY OF THE INVENTION

The present invention provides a modified yeast strain *Saccharomyces cerevisiae* having an accession number MCC 0069 and having properties of thermotolerance, osmotolerance, ethanol tolerance and self flocculation. In an embodiment of the present invention, the modified yeast strain having an accession number MCC 0069 is naturally selected and UV exposed.

An embodiment of the invention also includes methods of utilization of the modified strain of yeast *Saccharomyces cerevisiae* to produce enhanced amount of ethanol.

In other embodiment of the invention, the modified strain of yeast is thermotolerant.

In a further embodiment of the invention, the modified yeast strain is osmotolerant as it grows and ferments high concentration of sucrose and other mono- and disaccharides and produces high concentration/yield of ethanol, therefore is also ethanol tolerant.

In another embodiment of the invention, the modified strain of yeast is self flocculating.

In yet another embodiment of the invention, high ethanol production is achieved using modified yeast *Saccharomyces cerevisiae* strain at high temperature, high sugar concentration, and high ethanol concentration results in significantly decreased cost of input, improved downstream processing and reduction in affluent amount thus reducing the cost of affluent treatment.

In another embodiment of the invention, a method for obtaining the modified yeast strain comprises the steps of:
 a) subjecting strain of *Saccharomyces cerevisiae* to a temperature range of 45° C. to 47° C. and at 20% fermentable sugar concentration to obtain a selected strain; and
 b) treating said selected strain with Ultraviolet light to obtain the modified yeast strain.

In an embodiment of the present invention, a method is provided for ethanol production to be used as fuel, solvent, potable ethanol and for industrial application.

DETAILED DESCRIPTION OF THE INVENTION

Figure 1:
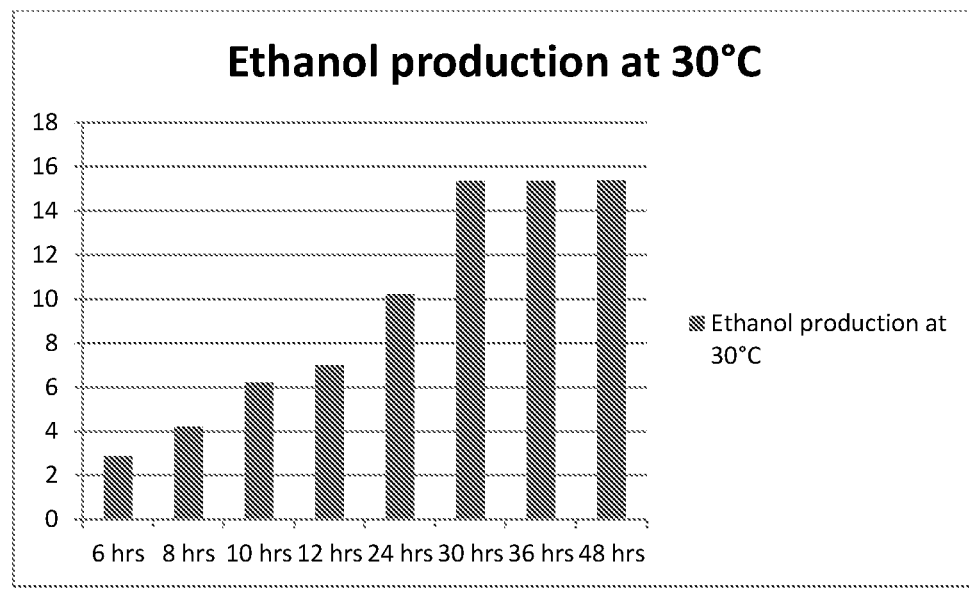
FIG. 1 relates to ethanol production at 30° C. using 20% sugarcane molasses by modified yeast wherein X axis represents incubation time in hours and Y axis represents ethanol percentage.
Figure 2:
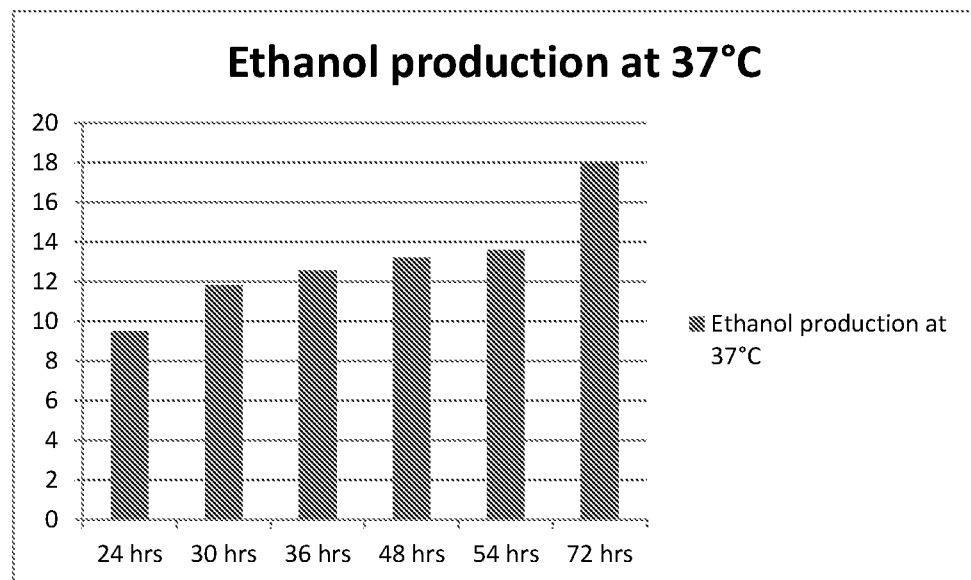
FIG. 2 relates to ethanol production at 37° C. using 20% sugarcane molasses by modified yeast wherein X axis represents incubation time in hours and Y axis represents ethanol percentage.
Figure 3:
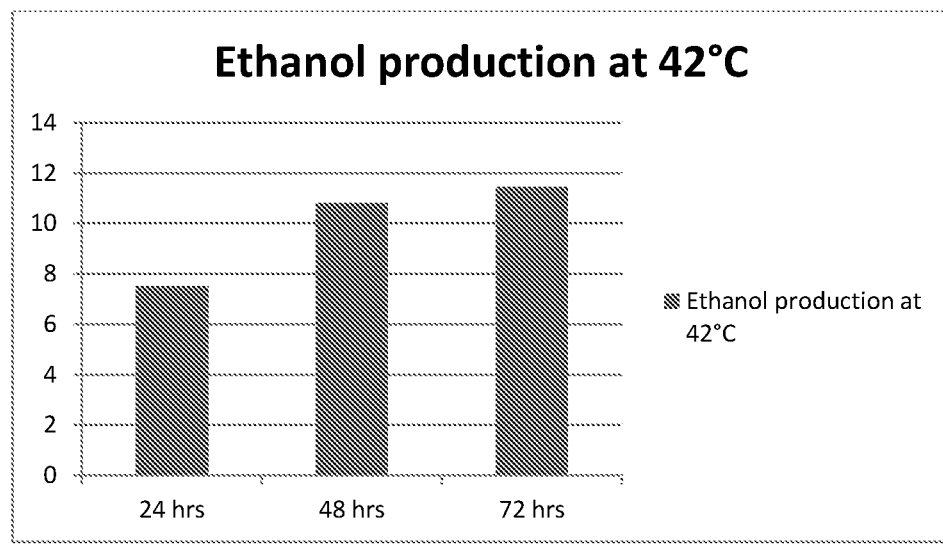
FIG. 3 relates to ethanol production at 42° C. using 20% sugarcane molasses by modified yeast wherein X axis represents incubation time in hours and Y axis represents ethanol percentage.
Figure 4:
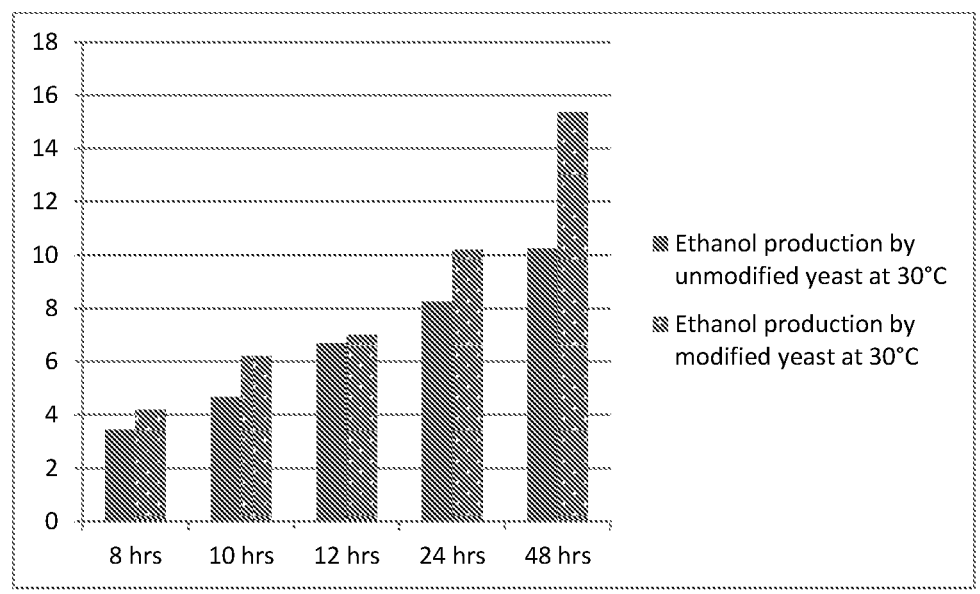
FIG. 4 relates to comparison of ethanol production by isolated strain of yeast and modified strain of yeast at 30° C. using sugarcane molasses as substrate at 8 hrs, 10 hrs, 12 hrs and 24 hrs of incubation. Series 1 represents unmodified isolated strain of yeast and series 2 represents modified strain of yeast. X axis represents time of incubation and Y axis represents ethanol percentage.
Figure 5:
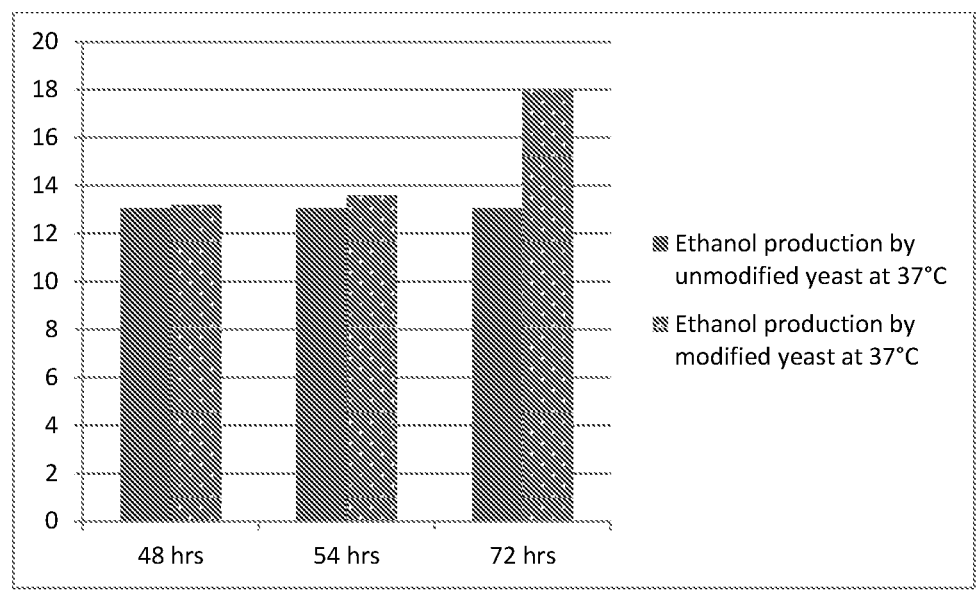
FIG. 5 relates to comparison of ethanol production by isolated strain of yeast and modified strain of yeast at 37° C. using sugarcane molasses as substrate at 48 hrs, 54 hrs and 72 hrs of incubation. Series 1 represents unmodified isolated strain of yeast and series 2 represents modified strain of yeast. X axis represents time of incubation and Y axis represents ethanol percentage.
Figure 6:
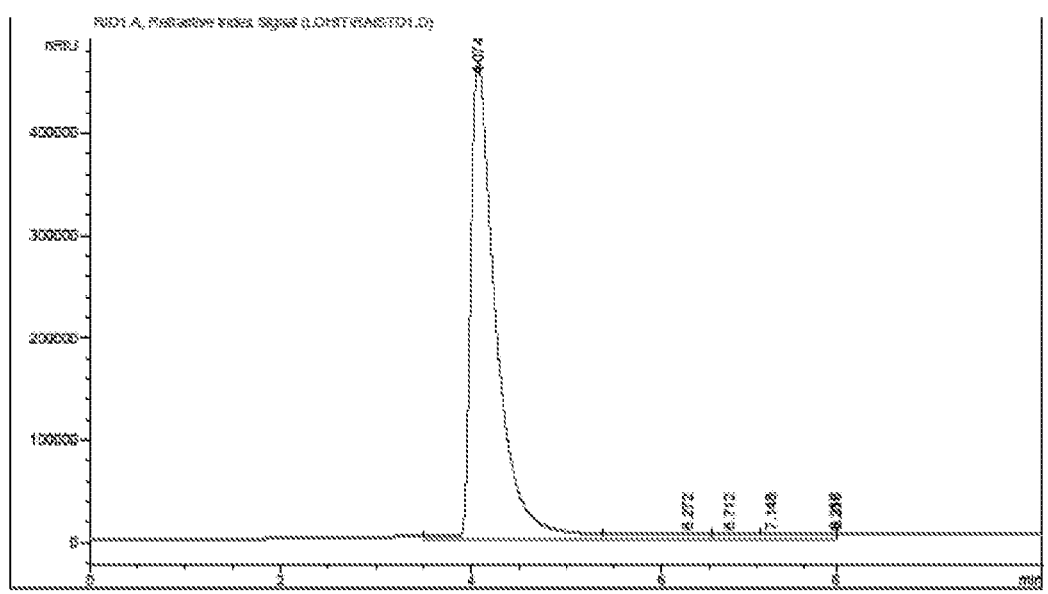
FIG. 6 shows a HPLC profile of ethanol produced in the present invention [HPLC profile shows ethanol production during fermentation of sugarcane molasses is almost free of any contamination].
Figure 7:
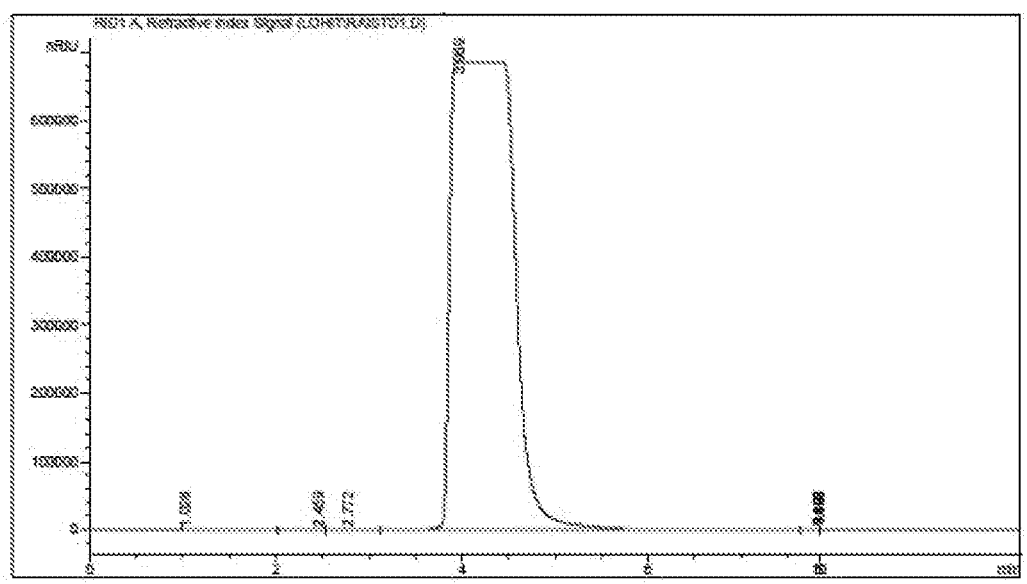
FIG. 7 shows the HPLC profile of pure ethanol.

It is to be noted that any terminology used in here is not to describe a particular embodiment only and is not limiting in its scope or otherwise. Examples are: use of singular forms "a", "an", and "the" can also include plural references unless it is clearly indicated or mentioned in the text. Any deviation is clearly indicated in the text. For example "an element" or "a method" could mean one or more element and one or more method. All units, prefixes and symbols may be denoted in their SI accepted form.

Numeric ranges as mentioned in the specifications are inclusive of the numbers defining the range and include each integer within the defined range.

Unless otherwise defined or indicated, all technical and scientific terms used in here have the same meaning as generally understood by one skilled in the art to which embodiments of this invention pertain. Many materials and methods similar or modified or equivalent to those described in here can be used while practicing the embodiments of this invention without doing any excessive experimentation of which preferred materials and methods as described in here. The headings provided while describing the embodiments and claims of the present invention, the headings are not a limitations to the embodiments of the present invention. The following terminology will be used in accordance with definitions described below.

The term "alcohol or ethanol producing microorganism" refers to any organism, including yeast, capable of fermenting and producing ethanol from any sugar source such as mono-, di- or oligo-saccharides originated from any source for example sugarcane, lignocellulosic material, grains or vegetables.

The term "fermentation" means enzymatic, anaerobic, semi-anaerobic or aerobic breakdown of organic substances by microorganisms in which process sugars are converted to ethanol, carbon dioxide (waste product) and cellular energy. Methods of fermentation and other steps or methods of ethanol production by fermentation (including separation of end product, distillation, purification and denaturation or dehydration of ethanol) are known and well documented in the art.

The term "osmotolerance" means a strain of yeast which can grow and produce ethanol from high concentrations of sugar, where the sugar can either be mono-saccharides, di-saccharides or any sugar present after saccharification of either lignocellulosic or starch from any source.

The term "saccharification" means conversion of starch or other lignocellulosic material in to sugars such as monosaccharides, disaccharides, oligosaccharides etc. by the action of enzymes. Methods of saccharification are well known in the art and can be performed by any one skilled in the art.

The term "ethanol (alcohol) tolerance" means ability of yeast to produce and be functional in the presence of high concentration of ethanol, such as producing ethanol in a medium containing high concentration of ethanol.

The term "thermotolerance" means an ability of a selected yeast strain to grow and remain functional such as ethanol production at high temperature.

The term "strain" means a functional yeast strain that is ethanol producing under the conditions described in this invention, or its mutants described in here, for example the strain of yeast *Saccharomyces cerevisiae*. The term functional yeast or mutants means, a strain of yeast directly or indirectly obtained by genetic modification including induced mutation either by using a chemical agent or ultraviolet light or by natural selection or spontaneous mutation, which may be achieved by any means or by using a referenced strain which retains ethanol tolerance, thermotolerance and sugar tolerance of the yeast strain *Saccharomyces cerevisiae*.

The term "yield", in general means the amount of end product such as various types of ethanol, including fuel ethanol, industrial ethanol or potable ethanol, produced during fermentation by the methods described in here by the way of examples and various embodiments. Yield may also refer to the concentration, volume, percentage or concentration of the end product in the fermentation broth, and by any other means of measuring the end product. The preferred end product measured in the present invention is alcohol and more precisely ethanol, which may be separated, purified and concentrated using the methods known to those skilled in the art. In some embodiments of the present invention the yield of ethanol using yeast strain *Saccharomyces cerevisiae* is in the range of 9% to 21.82% v/v ethanol including all the integers in between and fractions as described in this invention.

The ethanol produced by the present invention is used or as biofuel, solvent, potable ethanol and for industrial application.

Strain of Yeast

The present invention provides selected yeast strains from the Baster district of the state of Chhattisgarh, India and tested for improved/enhanced ethanol production over the currently used industrial strains of yeast and fermentation conditions used in India.

Yeast strain *Saccharomyces cerevisiae* was deposited at the Microbial Culture Collection, Pune, India, which is a recognized International Depositing Authority, under the Budapest Treaty provisions and has an accession number MCC 0069.

Yeast strain *Saccharomyces cerevisiae* was selected from a panel of twenty yeast strains isolated from fermenting plant extracts, having high level of dry matter. After significant number of experimentation, that is first purifying the yeast strain present in the fermenting plant materials, maintaining the pure culture in the laboratory, checking their growth at high temperature by inoculating the yeast strains in a untreated molasses containing fermentable sugar (depending upon the refining process of sugar from sugarcane juice which varies from factory to factory as well as region to region, at least in India). Dilutions were made in tap water, mixed with agar-agar, heated to dissolve the agar-agar and then plated on petri-plates (molasses in here can be autoclaved, if required). All the twenty natural isolates were further grown on a culture medium containing: Yeast extract, Peptone, Dextrose, Agar as and when required, (the medium will be known as YPD) and Glass distilled water. Serial dilutions of each of the natural isolates were prepared in sterile glass distilled water, optical density was measured and number of cells/ml at that optical density was counted by spreading them on YPD plates. To select a strain which is most tolerant to high temperature as well as sugar concentration in molasses, all the twenty isolates were separately suspended in sterile distilled water to obtain a cell number. Each of the isolate was spread on molasses plates. Twenty plates from each isolates were incubated at high temperature separately, until the growth was seen.

Out of twenty isolates originally selected for screening, seventeen did not show any growth at high temperature, thus were discarded. Three isolates which had an average number of colonies growing per plates were used for further investigations. However, the colonies were mixture of both small and large sizes, therefore, for the next set of experiments all the small size colonies were discarded. The large colonies selected in here were further plated on molasses plates as stated above and their growth was re-checked. Each of these colonies were suspended in YPD medium and spread on molasses plates as mentioned above to obtain single colony and also to recheck that they are not a mixture of small and large colony forming units of yeast cells and are stable clones. At this stage, out of three isolates selected for further study, two were discarded as the single colony from these two isolates produced once again a mixture of small and large colonies, indicating that these isolates were unstable on rigorous selection process (high temperature and high sugar concentration of molasses) used in here. In the present experimental set-up, each colony would originate from a single yeast cell and the experiments were designed to select for a mutant present in the population which would ferment high concentration of sugar to produce high amount of ethanol at high temperature. After re-plating, three colonies (now onwards referred as clones) which had shown good growth at high temperature on molasses plates were selected for further study. The repeat of growth studies with these clones as described earlier in here showed that all the three clones produced uniform size colonies which indicated that these clones were stable at high sugar concentration as well as high temperature. All the three clones were then tested for ethanol production from molasses without any supplementation. In here, again two of the clones were discarded because the alcohol production was low. The amount of alcohol produced by said two clones was ~12% alcohol at 37° C. and 40° C., whereas the third clone produced 14% alcohol both at 37° C. and 40° C. but there was about 7-8% residual sugar. Finally, only one clone was selected. $10 \times 10^6$ cells per ml in sterile distilled water from this clone (5 ml in a sterile petri plate with diameter of ~9 centimeters) were exposed to UV [ultraviolet] light and plated on molasses plate containing ~20% fermentable sugar at 45-47° C. Throughout the selection process unpurified molasses was used which contains very high amount of salts, other metals which may be toxic to many microorganism, sugars both fermentable and some amount of non-fermentable sugar.

Ten random colonies showing good growth were selected and tested for stability and ethanol production at high temperature and finally only one clone was selected and named as Devleela-1. The strain was identified as *Saccharomyces cerevisiae* and has been deposited at IDA, Microbial Culture Collection, Pune, India and has an accession number MCC 0069.

TABLE 1

Comparative data regarding properties of isolated strain of Saccharomyces cerevisiae, selected strain of Saccharomyces cerevisiae and UV exposed strain of Saccharomyces cerevisiae

| | Isolated strain of Saccharomyces cerevisiae | Selected strain of Saccharomyces cerevisiae | UV exposed strain of Saccharomyces cerevisiae |
|---|---|---|---|
| Thermotolerance | Growth in molasses up to 35° C. | Growth in molasses up to 45° C.-47° C. | Growth in molasses up to 45° C.-47° C. |
| Osmotolerance | Up to 10% fermentable sugar in molasses that came to about 40% molasses | More than 20% fermentable sugar. Molasses concentration up to 70% | More than 20% fermentable sugar. Molasses concentration up to 70% |
| Ethanol production | ~10-13% up to 35° C. | ~14% v/v up to 40° C. ~10% at 42° C. | ~16% v/v up to 40° C. ~12.8% at 42° C. |
| Re-use of inoculum after fermentation | Efficiency reduced after one use | Two times after that efficiency reduces | Five times without any change in efficiency |

UV exposed strain of Saccharomyces cerevisiae produced more alcohol than naturally selected strain of Saccharomyces cerevisiae, with almost zero percent of residual sugar and inoculum was used five times without change in efficiency of alcohol production. Since it produced more alcohol, it was also more ethanol tolerant than naturally selected strain of Saccharomyces cerevisiae.

Ethanol production was tested at different concentrations of fermentable sugar in molasses as well as at different temperatures separately. In the first set, ethanol production from fermentable sugar concentrations ranging from 6% to 15% at 25° C. was tested. Similarly, ethanol production was tested at other temperatures for example, 30° C., 33° C., 35° C. 37° C., 40° C., 44° C. and 45° C. The criteria for the selection were maximum ethanol production at temperature more than 30° C., preferably in minimum time. Ethanol production was also tested where seed culture was prepared by incubation at 170 rpm but after inoculation fermentation was continued in static condition at required temperature.

Ethanol fermentation was carried out in molasses diluted in tap water in a flask having different concentration of fermentable sugars which was autoclaved for 20 minutes at 120° C. First seed or starter culture was prepared by inoculating each of the three clones in different concentration of molasses separately and growing them for 18-20 hrs at 25-37° C. This starter or seed culture was used to inoculate the fresh molasses. The flasks were incubated at required temperatures, in a rotary shaker 170 rpm and ethanol production was tested after different time period. Entire fermentation broth was distilled and ethanol was collected. In this process, 50% of the original volume could be collected. Ethanol concentration was tested by potassium dichromate method. Residual fermentable sugar in each case was also tested by the DNS (di-nitrosalicylic acid) method. Out of the three clones selected for growth at 45° C., one of the clones failed to produce more than 12% v/v ethanol even at 30° C. thus was discarded. Though, the two clones produced more than 14% ethanol at 30° C., only one of them produced more than 14% v/v ethanol at temperatures more than 30° C. and was selected for further study. The strain was further tested by growth in molasses containing 20.6% fermentable sugar at 45° C. and for ethanol production. After confirming that the modified strain now available is stable, it was named as Devleela-1.

In embodiments of the invention, the enhanced ethanol producing method resulted in to increased alcohol yields were achieved by using modified yeast Saccharomyces cerevisiae as an ethanol producing micro-organism in the fermentation process.

Sugar and Ethanol Tolerance

In one of the embodiments, the modified strain of yeast shows growth at high concentration of sucrose containing other dry material which is present in the waste product of sugarcane industry that is sugarcane molasses as well as in the unpurified and undiluted or diluted sugarcane juice. The sucrose and other reducing sugars present in these fermentable media without any supplementation or in the presence of a source of nitrogen in the form of inorganic salts either as salts of ammonium or nitrate, urea, salts of magnesium, and salts of potassium or phosphates or magnesium is utilized by the modified strain to grow and be functional and convert these sugars into ethanol. The fermentable reducing sugars may vary from 5% to 35% in these media, specifically sucrose. However, the modified yeast strain could easily grow in untreated molasses concentration of 70% having reducing sugar of 45% at the temperature range of 30° C. to 45° C. The reducing sugar can either be monosaccharides or disaccharides or any other form of sugar.

Sustainable fermentation and high ethanol production at high temperature results in decreased expenditure as fermenters do not require cooling or chilling and other means which are generally being used to maintain the viability of yeast during fermentation. Therefore, it is economical, environment friendly and technically beneficial to use a thermotolerant strain of yeast in high concentration of ethanol production at high temperature.

Ethanol Production

According to the present invention ethanol or ethyl alcohol is the preferred end product during fermentation by the modified yeast strain from the claimed method described in here. In the preferred embodiments ethanol yield is in the range of 9% to 21.82% (v/v ethanol production). Ethanol yields obtained from the claimed method of this invention are identified by chemical methods as well as by high pressure liquid chromatography (HPLC) analysis. In the embodiments described in here, higher yield of ethanol results in lower input costs and higher economical realization from ethanol production.

The fermentation process of ethanol production is continued until sufficient yield of ethanol is produced. Fermentation process may be carried out for a period of 20 h to 80 h or longer. According to the present invention, a person skilled in the art will be able to ascertain any variable described in the present invention such as, sugar concentration in fermentation medium, length of fermentation or fermentation temperature to produce desired yield of ethanol by utilizing the modified yeast strain of *Saccharomyces cerevisiae*.

The invention provides a method for ethanol production and comprises of the modified yeast strain of *Saccharomyces cerevisiae*, medium containing sugars, particularly in a liquid medium. Culturing of modified yeast strain is conducted at a temperature which supports the growth and multiplication of the yeast as described in the present invention. In addition to at least one sugar, the medium may also contain more than one sugar, may or may not contain sources of nitrogen as inorganic or organic salts or any other source of nitrogen for example peptone, soyabean meals etc., amino acids or other chemical salts which supports the growth of the modified yeast strain. Suitable media include, for example, a media produced using sugarcane which is either sugarcane juice or molasses obtained at different stages of processing during cane-sugar production, with or without supplementing with source of nitrogen or other growth and multiplication supporting chemical salts or natural materials.

In one of the embodiments of the present invention high ethanol production is demonstrated by decreased amount of residual fermentable sugar levels. Lower residual fermentable sugar level is an indicator of rate and amount of ethanol production. An ideal ethanol production would be a condition where residual fermentable sugar is 0% and ethanol production is 100%, however, that is not possible as some amount of sugars will be used for the growth, multiplication and maintenance of microorganism.

Utilization of 100% of sugars enhances complete usage of substrates thus significantly decreasing the input cost of ethanol production.

Modified yeast strain of *Saccharomyces cerevisiae* yields higher ethanol and lower residual sugars due to increased conversion of sugar to ethanol. In a preferred embodiment of the present invention, residual sugar level is less than 1%, preferably 0.3% and more preferably 0.02%. The lower residual sugar level is achieved at temperatures greater than 30° C. and preferably greater than 35° C. or at 37° C. or at 40° C.

In yet other embodiment less or no stress during fermentation, though maintaining high sugar tolerance, high ethanol tolerance and high temperature tolerance was demonstrated where it was observed that glycerol is not produced during fermentation process by yeast strain. Glycerol production during ethanol fermentation is an indicator of stress where instead of ethanol, glycerol is produced. Modified yeast strain did not produce any glycerol in the temperature ranges described in this invention.

Embodiments of this invention are again defined in the non-limiting examples. It should be understood that these examples though indicate certain embodiments of the present invention, are provided only by way of illustrations. From the above discussions and the examples given in here, any person skilled in the art will be able to ascertain the essential characteristics of this invention and without departing from the spirit and scope of this invention can make various changes and modifications to the embodiments of the present invention to adapt it in to various usages and conditions.

EXAMPLES

Example 1

Method for Obtaining Modified Yeast Strain of *Saccharomyces cerevisiae*

A yeast strain of *Saccharomyces cerevisiae* was selected from a panel of twenty yeast strains isolated from fermenting plant extracts, having high level of dry matter. After significant number of experimentation, that is first purifying the yeast strain present in the fermenting plant materials, maintaining the pure culture in the laboratory, checking their growth at high temperature that is at 45° C.-47° C. by inoculating the yeast strains in a untreated molasses containing more than 20% fermentable sugar, molasses concentration can vary between 55%-60%. Here, the molasses received from the factory is considered as 100% and dilutions were made in tap water, mixed with 1.2% agar-agar, heated to dissolve the agar-agar and then plated on petriplates.

Yeast strains were directly selected for their growth in different concentration of molasses for examples from 10% to 70% molasses collected from different sugar mills around India. Fermentable sugar concentrations preferably sucrose along with other fermentable sugar in the molasses used in here varied from 45% to 60% depending upon the source of molasses. The concentration of molasses received from the sugar factory was considered as 100% and was diluted with water according to the need while also considering the concentration of fermentable sugars in the diluted or working concentration of molasses. The yeast strain described in here grows in unpurified molasses concentration of 70% which was diluted in water.

All the twenty natural isolates were further grown on a culture medium containing: Yeast extract (10 gram), Peptone (10 gram), Dextrose (10 gram), Agar (10 gram) as and when required, the medium will be known as YPD, Glass distilled water 1000 milliliter. Serial dilutions of each of the natural isolates were prepared in 1 ml sterile water, optical density at 600 nm (nanometer) was measured and number of cells/ml at that optical density was counted by spreading them in YPD plates. To select a strain which is most tolerant to high temperature as well as sugar concentration in molasses, all the twenty isolates were separately suspended in sterile distilled water to obtain a cell number $10^6$ cells/milliliter (ml). One hundred microliter of each of the isolate was spread on molasses plates where each plate had a diameter of ~9 centimeters. Twenty plates from each isolates were incubated at both 45° C. and 47° C. separately, until the growth was seen.

Out of twenty isolates originally selected for screening, seventeen did not show any growth at 45° C., thus were discarded. Three isolates which had an average 300 colonies growing per plates were used for further investigations. However, the colonies were mixture of both small and large sizes, therefore, for the next set of experiments all the small size colonies were discarded. The large colonies selected in here were further plated on molasses plates as stated above and their growth was re-checked. This process was repeated five more times (random number) and 10 colonies showing good growth from each of three original isolates were selected. Each of these colonies were suspended in one ml of YPD medium and spread on molasses plates as mentioned above to obtain single colony and also to recheck that they are not a mixture of small and large colony forming units of yeast cells and are stable clones. At this stage, out of three isolates selected for further study, two were discarded as the single colony from these two isolates produced once again a mixture of small and large colonies, indicating that these isolates were unstable on rigorous selection process (high temperature and high sugar concentration of molasses) used in here. In the present experimental set-up, each colony would originate from a single yeast cell and the experiments were designed to select for a mutant present in the population which would ferment high concentration of sugar to produce high amount of ethanol at high temperature. After re-plating, three colonies (now onwards referred as clones) which had shown good growth at both 45° C. and 47° C. on molasses plates containing 20% fermentable sugar were selected for further study. The repeat of growth studies with these clones as described earlier in here showed that all the three clones produced uniform size colonies which indicated that these clones were stable at high sugar concentration as well as at high temperature. All the three clones were then tested for ethanol production from molasses without any supplementation. In here, again two of the clones were discarded because the alcohol production was low.

Yeast strains growing at higher concentrations of molasses that is on and above 20% of molasses were screened for ethanol production using different concentration of molasses at 30° C. by chemical method (E. A. Crowell and C. S. Ough. Am. J. Enol. Vitic 1979, 30, 1, 61-63). 50 ml of molasses diluted in tap water in a 100 ml flask having different concentration of fermentable sugars were autoclaved for 20 minutes at 120° C. First seed or starter culture was prepared by inoculating each of the three clones in different concentration of molasses separately and growing them for 20 hrs at 30° C. This starter or seed culture was used to inoculate the fresh 50 ml molasses where final inoculum concentration was 10%. The flasks were incubated at required temperatures, in a rotary shaker 170 rpm and ethanol production was tested every 6.0 hrs till 72 hrs of incubation. Entire 50 ml fermentation broth was distilled and ethanol was collected. In this process, almost 50% recovery was achieved. Ethanol concentration was tested by potassium dichromate method. Residual fermentable sugar in each case was also tested by the DNS (di-nitrosalicylic acid) method.

Finally, only one clone was selected and $1 \times 10^6$ cells/ml from this clone, were exposed to UV [ultraviolet] light 12 ergs/mm$^2$ for 20 seconds to obtain 1.1% survival in a molasses plate containing 20% fermentable sugar at 45° C. Throughout the selection process unpurified molasses was used which contains very high amount of salts, other metals which may be toxic to many microorganism, sugars both fermentable and some amount of non-fermentable sugar.

Example 2

Ethanol Fermentation Using Molasses

The highest ethanol producing strain selected after observing growth at different concentration of molasses was then tested for ethanol production at different temperatures ranging from 25° C. to 44° C. In another experiment ethanol production was tested at different time period using optimum temperature where alcohol production was tested at different time period ranging after inoculations of 6 h, 12 h, 20 h, 24 h, 36 h, 40 h, 48 h, 54 h, 60 h, 66 h and 72 h up to 96 h. The modified strain of *Saccharomyces cerevisiae* produced maximum yield of ethanol.

Example 3

Preparation of Potassium Dichromate Reagent 0.5 gram potassium dichromate was dissolved in 5 ml of glass distilled water and the solution was kept in ice. After that 45 ml of concentrated sulfuric acid was added slowly with occasional mixing of the content. The solution was continued to cool in ice for another ~60 minutes and protected from light.

Example 4

Ethanol Estimation

One ml of ethanol sample/distilled product was mixed with one ml of potassium dichromate reagent and after thorough mixing the solution was placed in a water bath preset at 80° C. for 10 minutes. It was then cooled to room temperature and the optical density was recorded at 575 nm against a blank prepared with plain water. Alcohol concentration was calculated against a standard curve prepared using absolute ethanol.

Example 5

Estimation of Fermentable Sugar by Di-Nitrosalicylic Acid Method
Preparation of Di-Nitrosalicylic (DNS) Reagent In 100 ml of 1% sodium hydroxide solution made in distilled water, 1.0 gram di-nitrosalicylic acid, 200 milligram crystalline phenol and 50 milligram sodium sulfite was dissolved simultaneously by constant stirring. After all the ingredients were dissolved, the solution stored in dark until use. Take out volume of reagent separately just before use and add a pinch of sodium sulfite, mix well and use.

Example 6

Sugar Estimation Using DNS Reagent

Molasses was diluted to required concentration and one ml of the sample was mixed with one ml of DNS reagent and heated in a boiling water bath for 15 minutes. After cooling to room temperature, optical density was measured at 510 nm against blank prepared using water. Sugar concentration was calculated using a standard curve which was prepared using dextrose.

Example 7

Residual Fermentable Sugars Levels

Modified yeast strain showed low residual fermentable sugar and high ethanol production as adjudged by DNS methods (Miller, 1959, Analytical Chemistry, 31, 426-428).

Residual sugar level was less than 1% an indicative of high conversion of fermentable or reduced sugar to ethanol. HPLC analysis show some minor peaks which is less than 1% of the peak obtained for ethanol, indicating that almost all the fermentable sugar gets converted to ethanol. Residual sugar was lowest that is 0.02% at 37° C. and slightly more at 35° C. and 40° C. that is average 0.21%. Further, after completion of fermentation the residual sugar level was not detectable by the method used in this invention.

Though the present invention describes the ethanol production from sugarcane molasses and sugar cane juice, any other fermentable sugar such plant extracts or high sugar containing fruit juices etc. will be equally fine and it would be possible for any one skilled in the art to make various modifications in the methods described in here as examples and achieve similar results. Such modifications and changes of the sources of sugar are also intended to fall within the scope and spirit of appended claims.

TABLE 2

Residual sugar concentration after fermentation at 37° C.

| Sr. No. | Fermentation time | Total sugar concentration |
|---|---|---|
| 1 | 0 hour | 10.1% |
| 2 | 12 hours | 3.65% |
| 3 | 24 hours | 0.95% |
| 4 | 36 hours | 0.02% |
| 5 | 48 hours | Not detectable |

Total sugar of molasses was estimated after required fermentation time using standard DNS method.

Example 8

Ethanol Production by Unmodified Isolated Yeast Strain Using Sugarcane Molasses as Substrate a) Ethanol production by the "unmodified isolated" yeast strain at 30° C. Seed culture was prepared in 20% molasses for 20 hrs at 30° C. and 170 rpm. After inoculation flasks were removed at different time points and ethanol concentration was measured by dichromate method.

TABLE 3

Ethanol production by the "unmodified isolated" yeast strain at 30° C.

| Sr. No. | Time of incubation (in hrs.) | Ethanol percentage (%) |
|---|---|---|
| 1 | 6 | 3.12 |
| 2 | 8 | 3.45 |
| 3 | 10 | 4.68 |
| 4 | 12 | 6.68 |
| 5 | 24 | 8.25 |
| 6 | 48 | 10.24 | b) Ethanol production by the "unmodified isolated" yeast strain at 37° C. Seed culture was prepared in 20% molasses for 20 hrs at 30° C. and 170 rpm. After inoculation flasks were removed at different time points and ethanol concentration was measured by dichromate method.

TABLE 4

Ethanol production by "unmodified isolated" yeast strain at 37° C.

| Sr. No. | Time of incubation (in hrs.) | Ethanol percentage (%) |
|---|---|---|
| 1 | 6 | 6.86 |
| 2 | 8 | 7.52 |
| 3 | 10 | 8.25 |
| 4 | 12 | 10.0 |
| 5 | 24 | 12.75 |
| 6 | 48 | 13.06 |
| 7 | 54 | 13.06 |
| 8 | 72 | 13.06 | c) Ethanol production by the "unmodified isolated" yeast strain at 42° C. Unmodified isolated yeast strain growth was relatively poor at 42° C.

Example 9

Ethanol Production by Modified Yeast Strain Using Sugarcane Molasses as Substrate a) Ethanol production by the modified strain of *Saccharomyces cerevisiae*. Molasses was collected from local sugar factory and total sugar was estimated by standard DNS method. 100 ml flasks containing 50 ml molasses diluted (according to the sugar concentration present in the molasses from the factory) in tap-water, pH 4.5-5.2, and was sterilized by autoclaving. Each flask was inoculated using 20 h old 10% seed culture (prepared in the concentration of molasses to be used for fermentation 10% as final concentration of inoculum) and was incubated at 30° C. at 170 rpm. Two flasks were removed after each incubation time; ethanol was distilled and its concentration was estimated using potassium di-chromate method.

TABLE 5

Percent of ethanol in 20% sugarcane molasses at 30° C. & 170 rpm

| Sr. No. | Time of incubation (in hrs.) | Ethanol percentage (%) |
|---|---|---|
| 1 | 6 | 2.88 |
| 2 | 8 | 4.2 |
| 3 | 10 | 6.2 |
| 4 | 12 | 7.0 |
| 5 | 24 | 10.2 |
| 6 | 30 | 15.36 |
| 7 | 36 | 15.36 |
| 8 | 48 | 15.37 | b) Ethanol production by the modified strain of *Saccharomyces cerevisiae*. Molasses was collected from local sugar factory and total sugar was estimated by standard DNS method. 100 ml flasks containing 50 ml molasses diluted (according to the sugar concentration present in the molasses from the factory) in tap-water, pH 4.5-5.2, and was sterilized by autoclaving. Each flask was inoculated using 20 h old 10% seed culture (prepared in the concentration of molasses to be used for fermentation, 10% as final concentration of inoculum) and was incubated at 37° C. at 170 rpm. Two flasks were removed after each incubation time; ethanol was distilled and its concentration was estimated using potassium di-chromate method.

TABLE 6

Percent of ethanol in 20% sugarcane molasses at 37° C. & 170 rpm

| Sr. No. | Time of incubation (in hrs.) | Ethanol percentage (%) |
|---|---|---|
| 1 | 24 | 9.5 |
| 2 | 30 | 11.84 |
| 3 | 36 | 12.58 |
| 4 | 48 | 13.2 |
| 5 | 54 | 13.6 |
| 6 | 72 | 17.94 | c) Ethanol production by the modified strain of *Saccharomyces cerevisiae*. Molasses was collected from local sugar factory and total sugar was estimated by standard DNS method. 100 ml flasks containing 50 ml molasses diluted (according to the sugar concentration present in the molasses from the factory) in tap-water, pH 4.5-5.2, and was sterilized by autoclaving. Each flask was inoculated using 20 h old 10% seed culture and (prepared in the concentration of molasses to be used for fermentation, 10% as final concentration of inoculum) and was incubated at 42° C. at 170 rpm. Two flasks were removed after each incubation time; ethanol was distilled and its concentration was estimated using potassium di-chromate method.

TABLE 7

Percent of ethanol in 20% sugarcane molasses at 42° C. & 170 rpm

| Sr. No. | Time of incubation (in hrs.) | Ethanol percentage (%) |
|---|---|---|
| 1 | 24 | 7.5 |
| 2 | 48 | 10.8 |
| 3 | 72 | 11.44 |

Example 10

Ethanol Production by Modified Yeast Strain Using Sugarcane Juice as Substrate a) Ethanol production using sugarcane juice at 30° C. by the UV modified strain of yeast in presence of 0.5% Ammonium sulphate. Seed was prepared at 30° C. for 20 h at 170 rpm and then used for inoculation for fermentation. The flasks were incubated at 30° C., at 170 rpm, removed at different time points as indicated in the table below and alcohol concentration was measured by dichromate method.

TABLE 8

Percent of ethanol in sugarcane juice at 30° C. & 170 rpm

| Sr. No. | Time of incubation (in hrs.) | Ethanol percentage (%) |
|---|---|---|
| 1 | 12 | 8.97 |
| 2 | 20 | 10.5 |
| 3 | 24 | 12.16 |
| 4 | 30 | 13.2 |
| 5 | 36 | 14.76 |
| 6 | 48 | 15.13 | b) Sugarcane juice was purchased from a local vendor and was diluted to 20% in tap water and 0.5% ammonium sulphate (final concentration) was added to that. Ammonium sulphate was added as a source of nitrogen to support yeast growth. Seed was prepared at 30° C. for 20 h at 170 rpm and then used for inoculation for fermentation. The flasks were incubated at 37° C., at 170 rpm, removed at different time points as indicated in the table below and alcohol concentration was measured by dichromate method.

TABLE 9

Percent of ethanol in sugarcane juice at 37° C. & 170 rpm

| Sr. No. | Time of incubation (in hrs.) | Ethanol percentage (%) |
|---|---|---|
| 1 | 6 | 7.56 |
| 2 | 12 | 12.8 |
| 3 | 20 | 15.6 |
| 4 | 24 | 19.24 |
| 5 | 30 | 21.08 |
| 6 | 36 | 21.80 |
| 7 | 48 | 21.82 | c) Ethanol production using sugarcane juice at 42° C. by the UV modified strain of yeast in presence of 0.5% Ammonium sulphate. Seed was prepared at 30° C. for 20 h at 170 rpm and then used for inoculation for fermentation. The flasks were incubated at 42° C. at 170 rpm, removed at different time points as indicated in the table below and alcohol concentration was measured by dichromate method.

TABLE 10

Percent of ethanol in sugarcane juice at 42° C. & 170 rpm

| Sr. No. | Time of incubation (in hrs.) | Ethanol percentage (%) |
|---|---|---|
| 1 | 12 | 5.44 |
| 2 | 20 | 7.4 |
| 3 | 24 | 8.2 |
| 4 | 30 | 9.1 |
| 5 | 36 | 9.1 |
| 6 | 48 | 10.12 |

Example 11

Ethanol Production by the Modified Yeast Strain Using Rice as Substrate a) Ethanol production using rice as substrate: 100 g was treated with 120.00 U α-amylase, 85-90° C., 12 hours followed by 250.00 U gluco-amylase 55-60° C., 12 h. The mixture was then supplemented with magnesium sulphate (40 mg/100 ml), ammonium chloride (80 mg/100 ml), dipotassium hydrogen phosphate (140 mg/100 ml), yeast extract (40 mg/100 ml). Seed was prepared at 30° C. 170 rpm for 18 hours. Fermentation was conducted at 30° C., 170 rpm.

TABLE 11

Ethanol production at 30° C. using rice as substrate

| Sr. No. | Time of incubation (in hrs.) | Ethanol percentage (%) |
|---|---|---|
| 1 | 11 | 2.8 |
| 2 | 20 | 8.2 |
| 3 | 24 | 10.7 |
| 4 | 36 | 11.2 |
| 5 | 48 | 12.08 | b) Ethanol production using rice as substrate: 100 g rice was treated with 120.00 U of α-amylase, 85-90° C., 14 hours followed by 250.00 U of gluco-amylase at 55-60° C. for 11 h. The mixture was then supplemented with magnesium sulphate (40 mg/100 ml), ammonium chloride (80 mg/100 ml), dipotassium hydrogen phosphate (140 mg/100 ml) and yeast extract (40 mg/100 ml). Seed was prepared at 30° C., 170 rpm for 18 h. Fermentation was conducted at 37° C., 170 rpm. Ethanol concentration was tested by potassium dichromate method. Residual fermentable sugar in each case was also tested by the DNS (di-nitrosalicylic acid) method.

TABLE 12

Ethanol production at 37° C. using rice as substrate

| Sr. No. | Time of incubation (in hrs.) | Ethanol percentage (%) |
|---|---|---|
| 1 | 11 | 8.0 |
| 2 | 20 | 13.3 |
| 3 | 24 | 14.8 |
| 4 | 36 | 14.7 |
| 5 | 48 | 16.6 | c) Ethanol production using rice as substrate: 100 g was treated with 120.00 U α-amylase, 85-90° C., 12 hours followed by 250.00 U gluco-amylase 55-60° C., 12h. The mixture was then supplemented with magnesium sulphate (40 mg/100 ml), ammonium chloride (80 mg/100 ml), dipotassium hydrogen phosphate (140 mg/100 ml), yeast extract (40 mg/100 ml). Seed was prepared at 30° C. 170 rpm for 18 hours. Fermentation was conducted at 40° C., 170 rpm. Ethanol concentration was tested by potassium dichromate method. Residual fermentable sugar in each case was also tested by the DNS (di-nitrosalicylic acid) method.

TABLE 13

Ethanol production at 40° C. using rice as substrate

| Sr. No. | Time of incubation (in hrs.) | Ethanol percentage (%) |
|---|---|---|
| 1 | 11 | 2.8 |
| 2 | 19 | 11.2 |
| 3 | 24 | 14.7 |
| 4 | 35 | 14.4 |
| 5 | 43 | 14.08 | d) Ethanol production using rice as substrate: 100 g rice was treated with 120.00 U α-amylase, 85-90° C., 12 hours followed by 250.00 U gluco-amylase 55-60° C., 12 h. The mixture was then supplemented with magnesium sulphate (40 mg/100 ml), ammonium chloride (80 mg/100 ml), dipotassium hydrogen phosphate (140 mg/100 ml), yeast extract (40 mg/100 ml). Seed was prepared at 30° C. 170 rpm for 18 hours. Fermentation was conducted at 42° C., 170 rpm. Ethanol concentration was tested by potassium dichromate method. Residual fermentable sugar in each case was also tested by the DNS (di-nitrosalicylic acid) method.

TABLE 14

Ethanol production at 42° C. using rice as substrate

| Sr. No. | Time of incubation (in hrs.) | Ethanol percentage (%) |
|---|---|---|
| 1 | 11 | 4.92 |
| 2 | 20 | 9.1 |
| 3 | 24 | 10.01 |
| 4 | 35 | 10.75 |
| 5 | 44 | 9.7 |
| 6 | 48 | 8.6 |

Example 12

Ethanol Production by the Modified Yeast Strain Using Bajra as Substrate

Ethanol production using bajra as substrate after α-amylase treatment 1200 U at 85-90° C., 3 h followed by gluco-amylase 25000 U 55-60° C., 3 h. The mixture was then supplemented with magnesium sulphate (7 mg/100 ml), ammonium chloride (10 mg/100 ml), dipotassium hydrogen phosphate (50 mg/100 ml). Seed was prepared at 30° C. 170 rpm for 18 h and fermentation was done at 37° C., 170 rpm. Ethanol concentration was tested by potassium dichromate method. Residual fermentable sugar in each case was also tested by the DNS (di-nitrosalicylic acid) method.

TABLE 15

Ethanol production at 37° C. using bajra as substrate

| Sr. No. | Time of incubation (in hrs.) | Ethanol percentage (%) |
|---|---|---|
| 1 | 22 | 6.1 |
| 2 | 48 | 5.7 |
| 3 | 72 | 5.2 |

Example 13

Ethanol Production by the Modified Yeast Strain Using Maize Corn as Substrate

Ethanol production using maize corn after treatment with 1200 U α-amylase at 85-90° C., for 5 h followed by 200.00 U gluco-amylase at 55-60° C., for 18 hours (both commercial grade). Seed was prepared using respective substrates for 18 h at 30° C., 170 rpm. Fermentation was conducted at 37° C., 170 rpm. Ethanol concentration was tested by potassium dichromate method. Residual fermentable sugar in each case was also tested by the DNS (di-nitrosalicylic acid) method.

TABLE 16

Ethanol production at 37° C. using maize corn as substrate

| Sr. No. | Time of incubation (in hrs.) | Ethanol percentage (%) |
|---|---|---|
| 1 | 24 | 6.3 |
| 2 | 48 | 6.0 |
| 3 | 72 | 4.4 |

Example 14

Ethanol Production by the Modified Yeast Strain Using Banana Trunk Pulp as Substrate Ethanol production using Banana trunk pulp (Lignocellulosic substrate) as substrate. The pulp was supplemented with Ammonium chloride (50 mg/100 ml), Dipotassium hydrogen phosphate (80 mg/100 ml) and Magnesium sulphate (20 mg/100 ml), Yeast Extract (10 mg/100 ml), Calcium chloride (10 mg/100 ml). Seed was prepared in the pulp at 30° C. 170 rpm for 18 h. Fermentation conducted at 37° C. 170 rpm. Ethanol concentration was tested by potassium dichromate method. Residual fermentable sugar in each case was also tested by the DNS (di-nitrosalicylic acid) method.

TABLE 17

Ethanol production at 37° C. using Banana trunk pulp as substrate

| Sr. No. | Time of incubation (in hrs.) | Ethanol percentage (%) |
|---|---|---|
| 1 | 24 | 0.8 |
| 2 | 72 | 2.4 |

Advantages of the Invention

1. Modified yeast strain having properties of osmotolerance, ethanol tolerance, thermotolerance and self-flocculation.
2. High ethanol production using modified yeast *Saccharomyces cerevisiae* strain at high temperature, high sugar concentration, and high ethanol concentration results in significantly decreased cost of input, improved downstream processing and reduction in affluent amount thus reducing the cost of affluent treatment.

We claim:
1. A yeast strain resulting from exposure to ultraviolet light, the yeast strain being *Saccharomyces cerevisiae* having accession number MCC 0069, and having thermotolerance, ethanol tolerance, self flocculation and osmotolerance.

2. The yeast strain as claimed in claim 1, wherein said yeast produces ethanol at a temperature range from 25° C. to 44° C.

3. The yeast strain as claimed in claim 2, wherein said yeast produces ethanol at a temperature range from 37° C. to 42° C.

4. The yeast as claimed in claim 1, wherein said yeast produces ethanol in the range from 12.08% to 21.82% [v/v] using a substrate selected from the group consisting of sugarcane juice, sugarcane molasses, and rice at a temperature range of 30-42° C. for incubation time period in the range of 30-72 hours.

5. The yeast strain as claimed in claim 4, wherein said yeast produces ethanol in a range from 12.08% to 15.36% [v/v] using a substrate selected from the group consisting of sugarcane juice, sugarcane molasses, and rice at a temperature of 30° C. for incubation time period in the range of 30-48 hours.

6. The yeast strain as claimed in claim 4, wherein said yeast produces ethanol in a range from 16.6% to 21.82% [v/v] using a substrate selected from the group consisting of sugarcane juice, sugarcane molasses, and rice at a temperature of 37° C. for incubation time period in a range of 48-72 hours.

7. The yeast strain as claimed in claim 4, wherein said yeast produces ethanol in a range from 8.6% to 11.44% [v/v] using a substrate selected from the group consisting of sugarcane juice, sugarcane molasses, and rice at a temperature of 42° C. for incubation time period in a range of 48-72 hours.

8. The yeast strain as claimed in claim 4, wherein the sugarcane molasses used for the growth of said yeast is in a concentration in a range from 10% to 70%, and the amount of fermentable sugar concentration in said molasses is in the range from 45% to 60%.

9. The yeast strain as claimed in claim 1, wherein said yeast produces 3.2%-10.24% v/v of ethanol with a residual sugar level of less than 1% at temperatures greater than 30° C.

10. The yeast strain as claimed in claim 9, wherein said yeast produces 10-13% v/v ethanol with a residual sugar level of 0.3% at temperatures greater than 35° C.

11. The yeast strain as claimed in claim 10, wherein said yeast produces 9.5%-17.4% v/v ethanol with a residual sugar level of 0.02% at temperatures greater than or at 37° C.

12. A method for obtaining the yeast strain as claimed in claim 1, said method comprises the steps of:
 a) subjecting a strain of *Saccharomyces cerevisiae* to a temperature range of 45° C. to 47° C. and at 20% fermentable sugar concentration to obtain a selected strain; and
 b) treating said selected strain with ultraviolet light to obtain the modified yeast strain.

13. The method as claimed in claim 12, wherein the selected strain is exposed to ultraviolet light 12 ergs/mm² for 20 seconds to obtain 1.1% survival in a molasses plate containing 20% fermentable sugar at 45° C.

14. A method for the production of ethanol using a yeast strain of *Saccharomyces cerevisiae* having accession number MCC 0069, said strain having thermotolerance, ethanol tolerance, self flocculation and osmotolerance, wherein said method comprises the steps of:
 a) inoculating said yeast strain in a substrate selected from the group consisting of sugarcane molasses, sugar cane juice, plant extract, high sugar containing fruit juice, rice, bajra, maize corn, and banana trunk pulp to obtain a yeast culture;
 b) incubating said yeast culture for 6-96 hours at a temperature range of 25-45° C. at 150-170 rpm; and
 c) obtaining an amount of ethanol produced by said yeast culture after 24 hours of incubation.

15. The method as claimed in claim 14, wherein the temperature for the growth of said yeast is in a range from 35° C. to 40° C.

16. The method as claimed in claim 14, wherein the amount of ethanol produced by said yeast is in a range from 12.08% to 21.82% [v/v] using a substrate selected from the group consisting of sugarcane juice, sugarcane molasses, and rice at a temperature range of 30-42° C. for incubation time period in a range of 30-72 hours.

17. The method as claimed in claim 16, wherein the amount of ethanol produced by said yeast is in a range from 12.08% to 15.36% [v/v] using a substrate selected from the group consisting of sugarcane juice, sugarcane molasses, and rice at a temperature of 30° C. for a time period in a range of 30-48 hours.

18. The method as claimed in claim 16, wherein the amount of ethanol produced by said yeast is in a range from 16.6% to 21.82% [v/v] using a substrate selected from the group consisting of sugarcane juice, sugarcane molasses, and rice at a temperature of 37° C. for a time period of 48-72 hours.

19. The method as claimed in claim 16, wherein the amount of ethanol produced by said yeast is in a range from 8.6% to 11.44% [v/v] using a substrate selected from the group consisting of sugarcane juice, sugarcane molasses, and rice at a temperature of 42° C. for a time period in the a range of 48-72 hours.

20. The method as claimed in claim 14, wherein the sugarcane molasses used for the growth of said yeast is used in concentration in a range from 10% to 70%, and wherein the amount of fermentable sugar concentration in said molasses is from 45% to 60%.

21. The method as claimed in claim 14, wherein the ethanol obtained is used as biofuel, solvent, potable ethanol and for industrial application.

22. A yeast strain resulting from exposure to ultraviolet light, the yeast strain being *Saccharomyces cerevisiae* having accession number MCC 0069.

\* \* \* \* \*